US00PP13961P29

(12) United States Plant Patent
Utecht

(10) Patent No.: US PP13,961 P2
(45) Date of Patent: Jul. 8, 2003

(54) GERANIUM PLANT NAMED 'FIP 553'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,594

(22) Filed: Sep. 30, 2002

(51) Int. Cl.[7] ..... A01H 5/00

(52) U.S. Cl. ..... Plt./330
(58) Field of Search ..... Plt./330

*Primary Examiner*—Kent Bell
(74) *Attorney, Agent, or Firm*—Foley & Lardner

(57) ABSTRACT

A new and distinct cultivar of geranium plant named 'Fip 553' characterized by the combined features of deep red, semi-double flowers, large, full umbels at ideal height above the foliage, vigorous growth, well-branched, round plant habit and medium (mid season) spring flowering response.

1 Drawing Sheet

Latin name of the genus and species of the plant claimed: *Pelargonium zonale L'Héritier.*
Variety denomination: 'Fip 553'.

BACKGROUND OF THE INVENTION

The present invention comprises a new and distinct cultivar of geranium, botanically known as *Pelargonium zonale,* and hereinafter referred to by the cultivar name 'Fip 553'.

'Fip 553' is a product of a planned breeding program which had the objective of creating new zonal geranium cultivars with red flower color, medium green foliage and vigorous growth.

'Fip 553' originated from a hybridization made by the inventor Angelika Utecht in a controlled breeding program in Galdar, Gran Canaria, Spain, in 1995.

The female parent was an unpatented hybrid seedling, no. 91-1477-2, having orange-red single-type flowers, dark green foliage and medium sized plant habit. The male parent of 'Fip 553' was the patented variety 'Fissamba' (U.S. Plant Pat. No. 10,364), characterized by deep red flowers, and medium green foliage.

'Fip 553' was selected as one flowering plant within the progeny of the stated cross by Angelika Utecht in 1996 in a controlled environment in Galdar, Gran Canaria, Spain. The first act of asexual reproduction of 'Fip 553' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fip 553' are firmly fixed and are retained through successive generations of asexual reproduction.

'Fip 553' has not been observed under all possible environmental conditions. The phenotype may vary significantly with variations in environment such as temperature, light intensity and day length.

The following observations, measurements, and comparisons describe plants grown in Hillscheid, Germany under greenhouse conditions which approximate those generally used in commercial practice.

BRIEF SUMMARY OF THE INVENTION

The following traits have been repeatedly observed and are determined to be basic characteristics of 'Fip 553' in combination distinguish this geranium as a new and distinct cultivar:

1. Brilliant, deep red, semi-double flowers;
2. relatively large, many-flowered inflorescences, well above the foliage;
3. medium-green foliage with medium zonation;
4. vigorous growth, bushy and rounded plant habit; and
5. medium (mid season) spring flowering response. Of the many commercial cultivars known to the present inventor, the most similar in comparison to 'Fip 553' is the parental variety 'Fissamba', and the variety 'Fisrored' (U.S. Plant Pat. No. 12,917).

In comparison to 'Fissamba', 'Fip 553' has very similar flowers, with respect to both color and shape, but much more vigorous growth habit. By the end of the summer, plant diameter of 'Fip 553' was roughly twice the size of plants of 'Fissamba'.

In comparison to 'Fisrored', 'Fip 553' has even slightly deeper red general flower color, rounder, not flat, inflorescences, slightly less distinct leaf zonation, and somewhat taller plant habit.

BRIEF DESCRIPTION OF THE DRAWING

The accompanying photographic drawing shows typical flower and foliage characteristics of 'Fip 553' with colors being as true as possible with an illustration of this type. The drawing depicts side elevational view of a typical flowering potted plant of 'Fip 553'.

DETAILED BOTANICAL DESCRIPTION

The measurements were taken in Hillscheid, Germany in mid May 2002, 10 weeks after planting of rooted cuttings. The plants were grown in 14 cm pots, they had not been pinched.

In the following description color references are made to The Royal Horticultural Society Colour Chart. The color values were determined indoors from flowers developed in a green-house in May 2002 in Hillscheid, Germany.

Inflorescence:

*Type.*—Umbel, semi-spherical to between semi-spherical and spherical.

*Average diameter.*—130 mm.

*Average depth.*—90 mm.

*Peduncle length.*—190 mm.

*Peduncle color.*—Light green, RHS 143 B, partly brownish infused, RHS 181 B.

*Pedicel.*—38 mm in length.

*Pedicel color.*—Mainly red-brown, RHS 181 A, near base green, RHS 144B.

*Number of flowers per umbel.*—About 40–50.

Corolla:

*Average diameter.*—45 mm.

*Form.*—Semi-double.

*Shape.*—Round outline with the upper petals about the same size as the lower petals, weakly cup-shaped.

*Number of petals.*—6–8.

*Number of petaloids.*—0–1.

*Shape of petals.*—Obovate, base acute, upper end is truncate or rounded, margin is entire.

*Size of petals.*—Upper petals: 24–26 mm long, 22–24 mm wide lower petals: 22–24 mm long, 24–25 mm wide.

*Color (general tonality from a distance of three meters).*—Deep red.

*Color of upper petals.*—RHS 45 B.

*Markings of upper petals.*—Two fine, dull purple veins, RHS 185 B.

*Color of lower petals.*—RHS 45 B.

*Markings of lower petals.*—Absent.

*Color of lower surface of petals.*—RHS 44 B.

*Color of sepals.*—Outer surface: mainly red-brown, RHS 181 A, tips: green RHS 137 D; inner surface: mainly RHS 180 B, tips RHS 144 B.

*Number of sepals.*—5.

*Shape of sepals.*—Linear to lanceolate, acute tip, truncate base, surface with very weak pubescence, margin entire.

*Size of sepals.*—10–12 mm long, 4 mm wide for the largest upper sepal, 2–3 mm in width for the other sepals.

Bud (just prior to petals unfolding):

*Shape.*—Elliptical.

*Color of sepals.*—Light green, RHS 143 B, base reddish RHS 179 A.

*Color of petals.*—RHS 44 A.

*Length.*—17 mm.

*Width.*—10 mm.

Reproductive organs:

*Androecium.*—5–7 fertile anthers, moderate pollen, yellow-orange, RHS 26 A, filaments white, RHS 155 D, to light-pink, RHS 52 D.

*Gynoecium.*—One pistil, stigma 5–6-lobed, style and stigma dark-red, RHS 53 A.

*Fertility/seed set.*—No seed set observed.

Spring flowering response period: In Hillscheid, Germany, in 2002 plants had on average 0.4 flowers opened 10 weeks after planting of rooted cuttings. Outdoor flower production: Continuously flowering with a fair number of inflorescences, the flower count in 2002 in Hillscheid, Germany, indicated about 3.0 inflorescence per plant in mid May.

Durability: Good stability of flower color, but somewhat susceptible to being scorched by the sun (typical for the deep red color group), good rain resistance.

Lastingness of the individual flower: About 8 days at 18° C., about 17–19 days for the umbel.

Fragrance: None.

PLANT

Foliage:

*Shape.*—Kidney-shaped with very weak lobes, cordate base, with the gap between the lowest lobes open.

*Margin.*—Bi-crenate, somewhat wavy. Texture: Upper surface smooth, velvety.

*Size of leaf.*—105 mm wide, 63 mm long.

*Color of upper surface.*—Medium green, approximately RHS 137 C.

*Color of zonation.*—Brown, about RHS 166 A, medium distinct.

*Color of lower surface.*—RHS 137 D.

*Petioles.*—50–60 mm long, 3–3.5 mm diameter, light green in color, approximately RHS 143 C.

General appearance and form:

*Stem color.*—Grass green, RHS 143 A to 143 B.

*Internode length.*—20–25 mm.

*Branching pattern.*—7.0 branches.

*Size of plants.*—Height: 22.0 cm, width: 38.5 cm (10-week-old plants, as described, measured from the top of the soil (base of the main stem) to the tips of the branches, without inflorescences).

Pest/Disease Resistance/Susceptibility: No observations to date.

I claim:

1. A new and distinct cultivar of geranium plant named 'Fip 553', as described and illustrated herein.

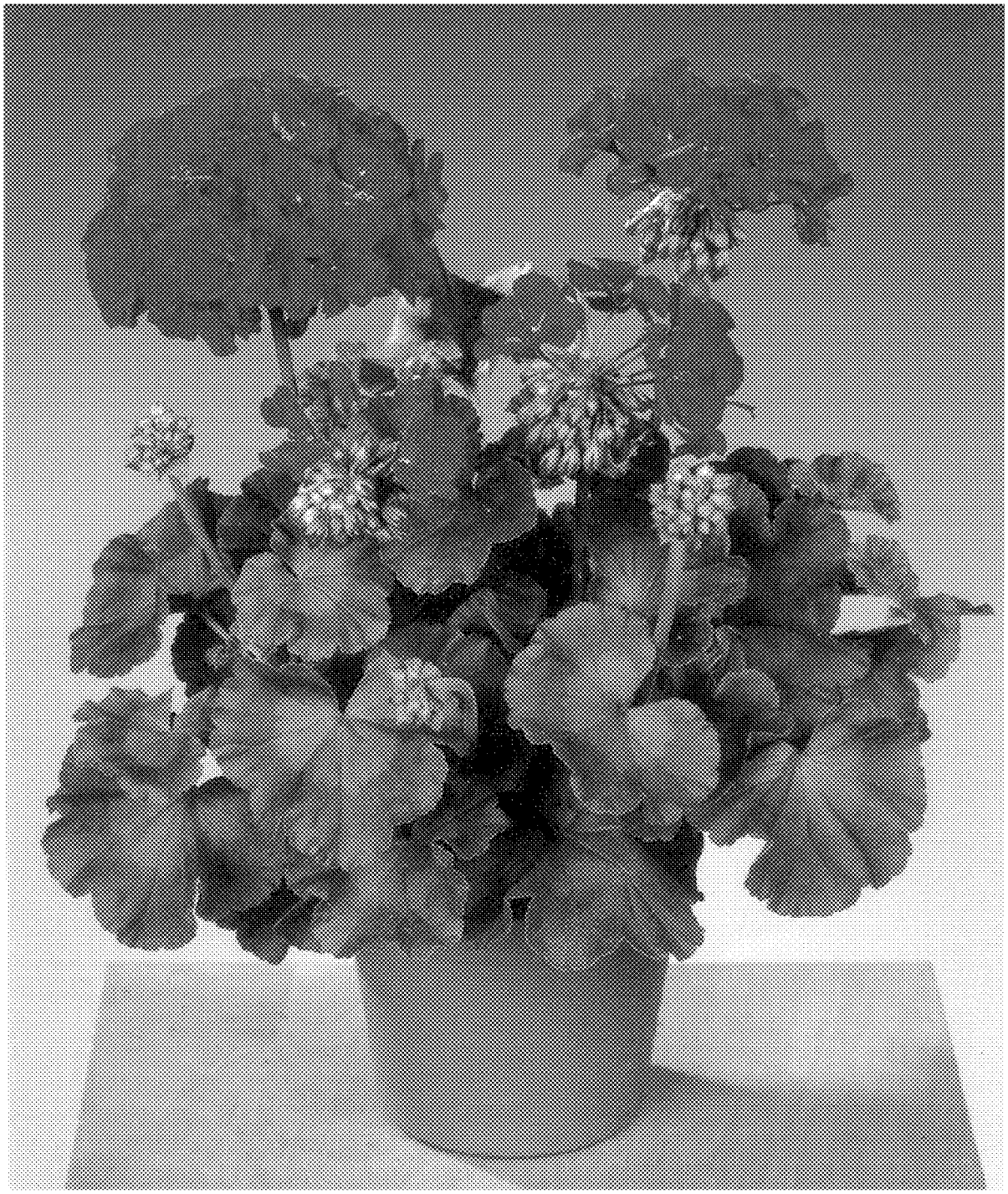

* * * * *